United States Patent [19]

Marques et al.

[11] Patent Number: 4,716,895
[45] Date of Patent: Jan. 5, 1988

[54] ARM SLING

[76] Inventors: Jean S. Marques, 10341 Jackson Hole Rd., Palo Cedro, Calif. 96073; Ernesto D. Marques, 23841 Kara Bay, Laguna Niguel, Calif. 92677

[21] Appl. No.: 619,206

[22] Filed: Jun. 11, 1984

[51] Int. Cl.⁴ .............................................. A61F 5/40
[52] U.S. Cl. ...................................................... 128/94
[58] Field of Search ........................... 128/94, 87 R, 77

[56] References Cited

U.S. PATENT DOCUMENTS

| | | | |
|---|---|---|---|
| 1,490,381 | 4/1924 | Gobar | 128/94 |
| 1,808,422 | 6/1931 | MacDonald | 128/94 |
| 1,991,677 | 2/1935 | Jacks | 128/94 |
| 2,306,715 | 12/1942 | Rubinstein | 128/94 |
| 2,460,589 | 2/1949 | Lewis | 128/94 |
| 2,594,809 | 4/1952 | Sanders | 128/94 |
| 3,371,663 | 3/1968 | Apgar | 128/94 |
| 3,515,131 | 6/1970 | Stevens | 128/94 |
| 4,214,579 | 7/1980 | Ford | 128/94 |
| 4,437,459 | 3/1984 | Slavetskas | 128/94 |
| 4,598,666 | 7/1986 | Spanko | 119/106 |

Primary Examiner—Robert P. Swiatek
Assistant Examiner—David L. Tarnoff
Attorney, Agent, or Firm—Richard L. Gausewitz

[57] ABSTRACT

A sling for support of the arm, comprising an elongated cloth body having a relatively wide central region and relatively narrow end regions, and further having an arm extending outwardly from adjacent the central region. The body is mounted on one shoulder and supports the opposite arm, without the need for any separate arm-containing pouch or pocket. Hook and loop fasteners are provided to secure the ends of the body to each other, and to secure the arm to the body.

21 Claims, 7 Drawing Figures

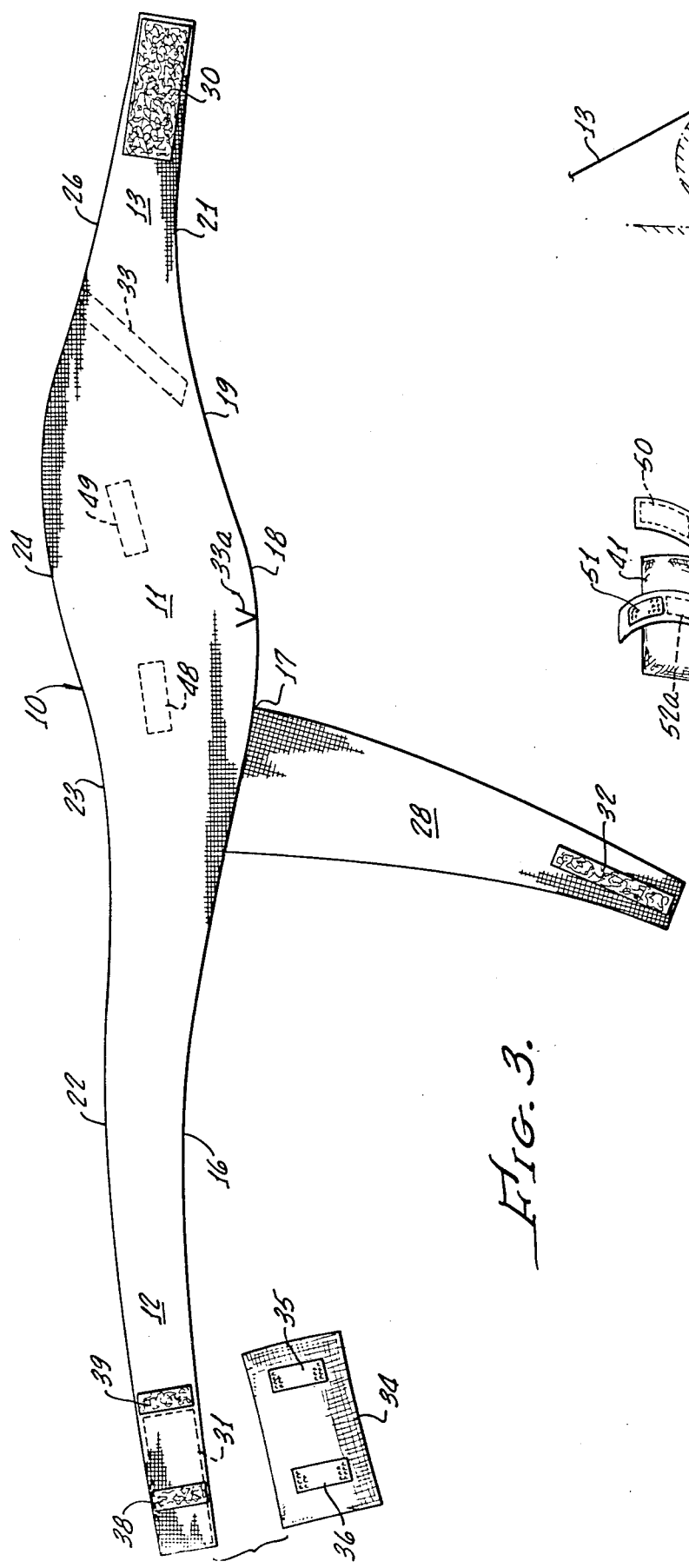
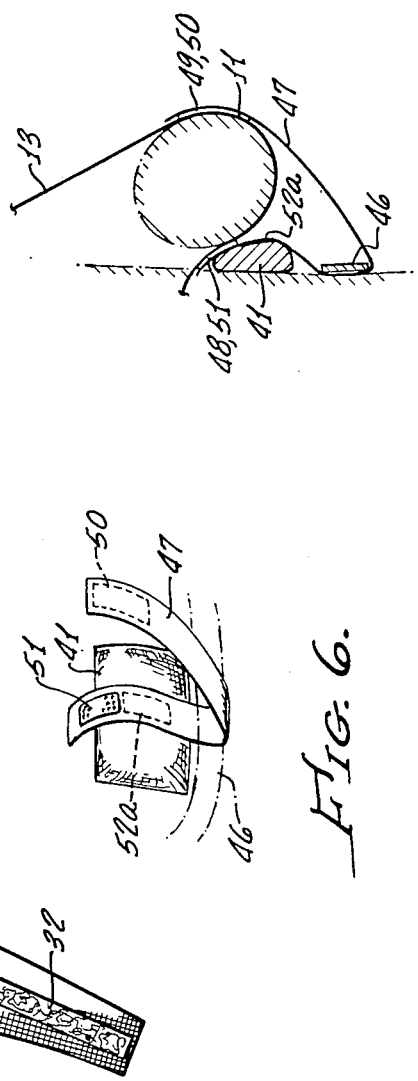

ARM SLING

BACKGROUND OF THE INVENTION

This invention relates to the type of arm sling used primarily for injuries or diseases relating to the shoulder girdle (the muscles and bones—such as the humerus—at or connecting to the shoulder region). Such injuries or diseases include fractures, dislocations, bone cancer, and the like. The arm sling supports the arm so that it does not exert weight on the injured or diseased region. Arm slings of the present type are also frequently employed relative to arms that are paralyzed, to prevent them from dangling and flopping. The indicated type of sling is to be distinguished from the ones that were formerly—and are sometimes presently—employed for treatment of shoulder separations.

Slings of the type here discussed are often characterized by lack of comfort, by unsightliness, by difficulty of mounting and adjustment, and by inability to achieve adequate adjustment, support or immobilization. Such slings are particularly onerous when the wearer must wear them for long periods of time, such as for months or even years.

The classical Boy Scout sling (which is similar to the slings made by sailors in the days when sailors wore neckerchiefs extensively), is also characterized by discomfort and inadequate support. A Boy-Scout sling goes around the neck, that is to say, rests on top of both shoulders on opposite sides of the neck. It is, at best, a temporary expedient.

SUMMARY OF THE INVENTION

Applicants have discovered that a sling, preferably made from a few pieces of cloth, but which does not go around the neck and/or rest on both shoulders, is surprisingly effective, comfortable, adjustable, easy to mount and remove, simple to adjust, etc. The sling holds its shape, does not bite into the body of the wearer at any point, and is attractive looking as distinguished from clinical-looking.

Furthermore, the present sling has a second portion which, in a few seconds, can be adjusted to ensure that the forearm will not slide out of the underlying supporting portion of the sling.

Once the sling is adjusted for any wearer, it may be removed and repositioned without necessity for disconnection of any fastener, and without necessity for further adjustment. The sling is readily washed, perferably in its adjusted condition, which achieves the further benefit that the long secton of cloth does not wrap around the agitator portion of the washer.

The second portion of the string performs the additional function of aiding in initial mounting and adjustment.

In addition to the above, the present invention provides pillow or other supporting means at the shoulder, and (soon after surgery, for example) between the forearm and the stomach region of the wearer. Means are also provided to connect the sling to a belt or belt loop, in order to achieve an added degree of immobilization.

A major characteristic of the sling is that an edge, which is uppermost when behind the body, curves around the side of the body adjacent the arm being supported, and then becomes lowermost. Such edge then passes under the arm of the wearer at a location adjacent the wrist. It then bends upwardly and defines one side of a sling portion which extends upwardly across the chest to the shoulder on which the sling is supported. Another feature of the invention relates to a major adjustment and connecting means located at or near the shoulder region. Such asjustment and connecting means also operates as an indicator to show the patient, or a person aiding the patient, exactly how to put the sling on. Another indicia is provided at the midregion of the sling, to show the patient (or an assistant) where the elbow should be located.

BRIEF DESCRIPTION OF THE DRAWINGS

FIG. 3 is a plan view showing the sling when disposed in a single plane;

FIG. 6 shows the optional pillow or cushion which goes between forearm and stomach; and FIG. 7 is a side elevational view illustrating the pillow of FIG. 6, the forearm being shown, by phantom lines, in section.

DETAILED DESCRIPTION OF THE PREFERRED EMBODIMENTS

Figure 1:
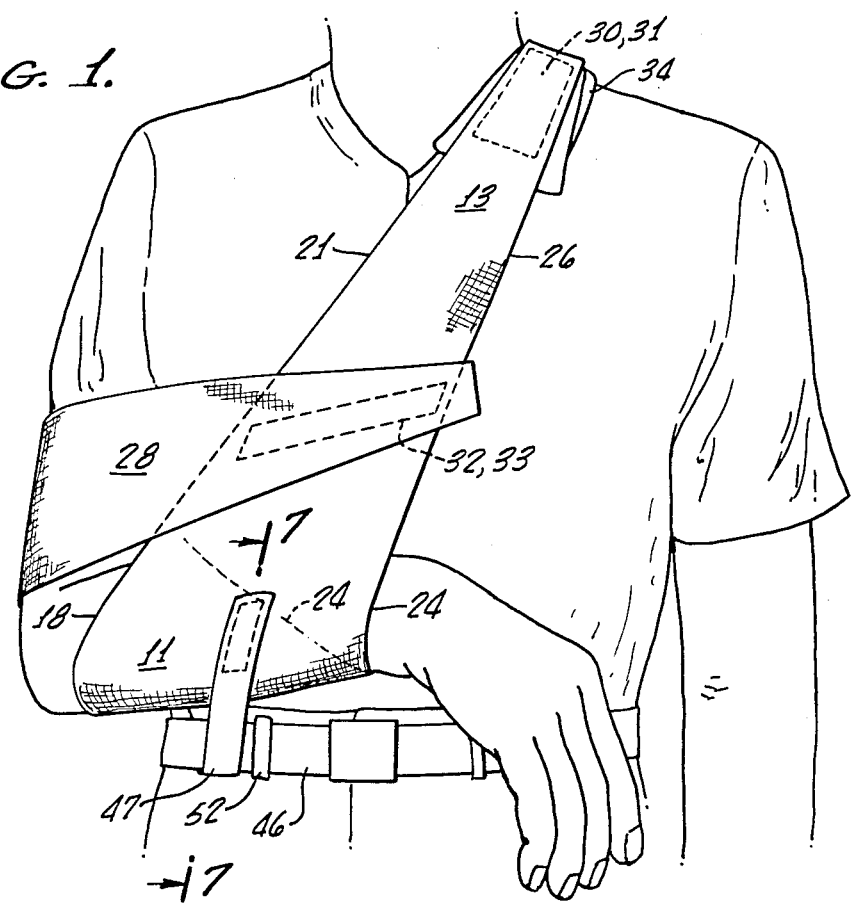
FIG. 1 is a front elevational view showing the sling mounted on a patient, and further showing the optional means which extends around the belt of the patient and connects to the supporting region of the sling.

In the preferred embodiment, hook and loop fastener and adjustment means, such as the one having the brand name VELCRO, are employed. Furthermore, to aid in the description, one portion of each fastener will be described as the one having (or being) the "hook", while the other will be described as the one having (or being) the "loop". It is emphasized, however, that these may, in practice, be interchanged, and that the indicated convention is merely used to aid in the description of the invention.

The entire sling, excepting only the fastener means, is preferably formed of cloth. As a preferred example, each portion of the sling comprises two parallel layers of soft but strong cloth, the layers being seamed together at the edge regions and with the edges bent inwardly so as to prevent fraying.

The layers of the two cloths should be sewn so that the bottom side of the sling is cut on the width of the material, and the top side is cut on the length of the material. This prevents a "creeping effect". In other words, the woof threads extend longitudinally of the body 10, as shown in FIG. 3, on the bottom side of the sling. Conversely, in the top layer of the material, as shown in FIG. 3, the warp threads extend longitudinally of the body 10.

Referring to FIG. 3, the sling comprises a single elongated body 10 having a relatively wide intermediate region 11 adapted to receive the forearm of the patient, and also having two relatively narrow connector regions 12 and 13 that extend in opposite directions away from the intermediate region. Connector region 12 is relatively long, while connector region 13 is relatively short.

The shapes of the edges of the illustrated preferred form will next be described, all in reference to FIG. 3 which shows the apparatus when lying flat. (Thus, when the invention is described in reference to FIG. 3, such words as "lower" and "upper" relate to that figure only, having no reference to elevation when the sling is on the patient).

Lower edge 16 of connector region 12 is very gradually concave, and the concavity continues to the vicinity of point 17. At or relatively near such point, there starts a convex lower edge 18 of intermediate region 11 of the sling. The degree of convexity of edge 18 is substantially greater than is the degree of concavity of edge 16. Convex edge 18 continues to the vicinity of point 19, at which there starts the gradually concave lower edge 21 of connector region 13.

To summarize, therefore, the lower edge of the elongated body is preferably gradually concave at connector regions 12 and 13, and less-gradually convex at intermediate region 11.

The upper edge, numbered 22, of connector region 12 is gradually convex, and diverges toward the right in relation to the lower edge 16 of such region. In the vicinity of point 23, the convex edge 22 meets a second and much more prominent convex upper edge which is numbered 24. Convex edge 24 forms the upper edge of intermediate region 11, and is much more elevated than is upper edge 22 of connector region 12. Convex edge 24 merges toward the right with the upper edge 26 of connector region 13, such upper edge being relatively straight or slightly concave.

The most prominent or "peak" region of edge 24 is offset, toward the right, relative to the most prominent portion of edge 18. Edges 21 and 26 converge to the right, relatively rapidly, because connector region 13 is much less long than is connector region 12 which has the gradually diverging (toward the right) edges 16 and 22.

The two convex edges 22 and 24 define between them a concave region generally adjacent point 23. Edges 22, 24 and 26 connect smoothly to each other, as do edges 16, 18 and 21.

Still referring to FIG. 3, a laterally-projecting arm 28, also preferably formed of cloth, is seamed to the elongated body 10 at a region between concave edge 16 and convex edge 18. Stated otherwise, the arm 28 is seamed to the lower body edge generally at the junction between intermediate region 11 and connector region 12. In the illustrated form, the right side of arm 28 intersects the lower edge of the body in the vicinity of point 17.

As illustrated, arm 28 is less long than connector region 12, but longer than connector region 13.

The lengths of body 10 and arm 28 vary in accordance with the size of the patient, for example coming in children's, small, medium, large, and extra large sizes. There need not be an infinite number of size variations, because the fastener means described below permit substantial degrees of adjustment.

Proceeding next to a description of the fastener and adjustment means, there is a relatively long section 30 of loop at the outer end of connector region 13, and on the top side of the body 10 as viewed in FIG. 3. A corresponding hook section 31 is mounted at the outer end of connector region 12 and on the underside of body 10 as viewed in FIG. 3.

To connect and adjust the arm 28, a relatively long strip 32 of loop is mounted at the outer end of arm 28 and on the upper side thereof, as shown in FIG. 3, the strip extending longitudinally of the arm and spaced inwardly from both edges thereof. A strip 33 of hook is mounted transversely on the underside of body 10, at the connector region 13 of such body. The strip 33 inclines upwardly and toward the right, as viewed in FIG. 3, and is oriented to mate with loop 32 when the sling is in mounted condition.

Reference will next be made, primarily, to figures other than FIG. 3. For simplicity of description, the word "patient" will be used, although it is recognized that in most or many instances a nurse or aide will actually perform the function because of the disability of the patient.

To mount and adjust the sling as thus far described, without becoming confused, the patient requires only two (or, for many, only one) indicia or reference points. One is the hook 31; the other is a marker 33a (illustrated to be a "V" sewn on the upper side of body portion 11, as viewed in FIG. 3) between arm 28 and the "peak" of lower edge 18 as viewed in FIG. 3.

Assuming that it is the right arm which requires support, the hook 31 is disposed on the left shoulder and facing upwardly, it being emphasized that the body 10 is then hanging behind the body of the patient. Stated otherwise, body 10 of the sling is in a generally vertical orientation behind and adjacent the patient's body when the patient is standing, and the end of connector portion 12 is bending forwardly over the left shoulder of the patient with the hook means 31 facing upwardly (exposed).

To ensure that the cloth body will not twist, the patient grasps arm 28 at its outer end, using his right hand, and keeps such arm 28 horizontally by effecting a slight pulling action toward the right. This also pulls the pendent body 10 to the right, and exposes the loop 30 to the patient's view. The patient then grasps the lower end of region 13 with his left hand, and releases arm 28 with his right. He then places his right elbow on the indicia 33a at intermediate region 11, while bending connector region 13 upwardly-forwardly of his horizontal right forearm. The loop 30 is then moved upwardly (by means of the left hand) and pressed against hook 31 to form a connection near the shoulder as shown in FIGS. 1 and 4.

Figure 4:
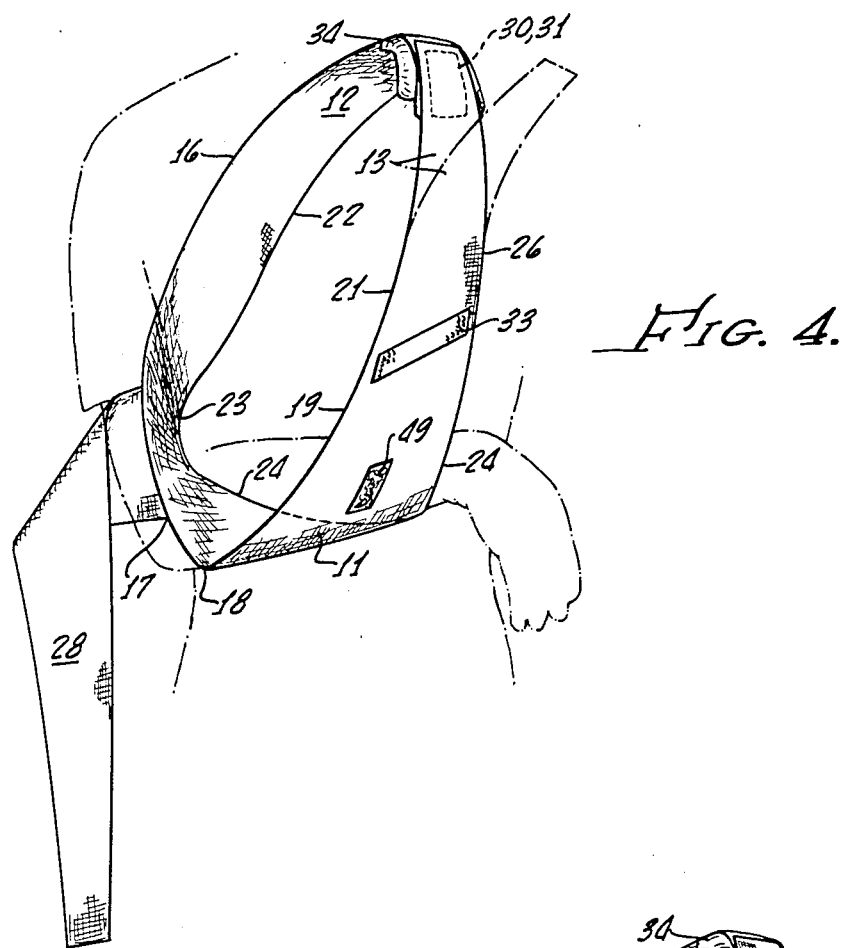
FIG. 4 shows the first part of the sling-mounting procedure (for a sling that has not yet been adjusted to a patient), the body of the patient being indicated in FIG. 4 (and also FIG. 5) in phantom line, so that the patient's body is treated as being transparent.

The right forearm of the patient is thus effectively suspended as shown in FIGS. 1 and 4. The right elbow is near the indicia 33a. It is emphasized that the showings of FIGS. 1 and 4 illustrate the inclined edge region 24. Such edge region is disposed between the forearm and the body of the patient. Stated otherwise, the edge 24 is behind the forearm, and forms the upper edge of that region 11 of the sling which supports the forearm.

Figure 2:
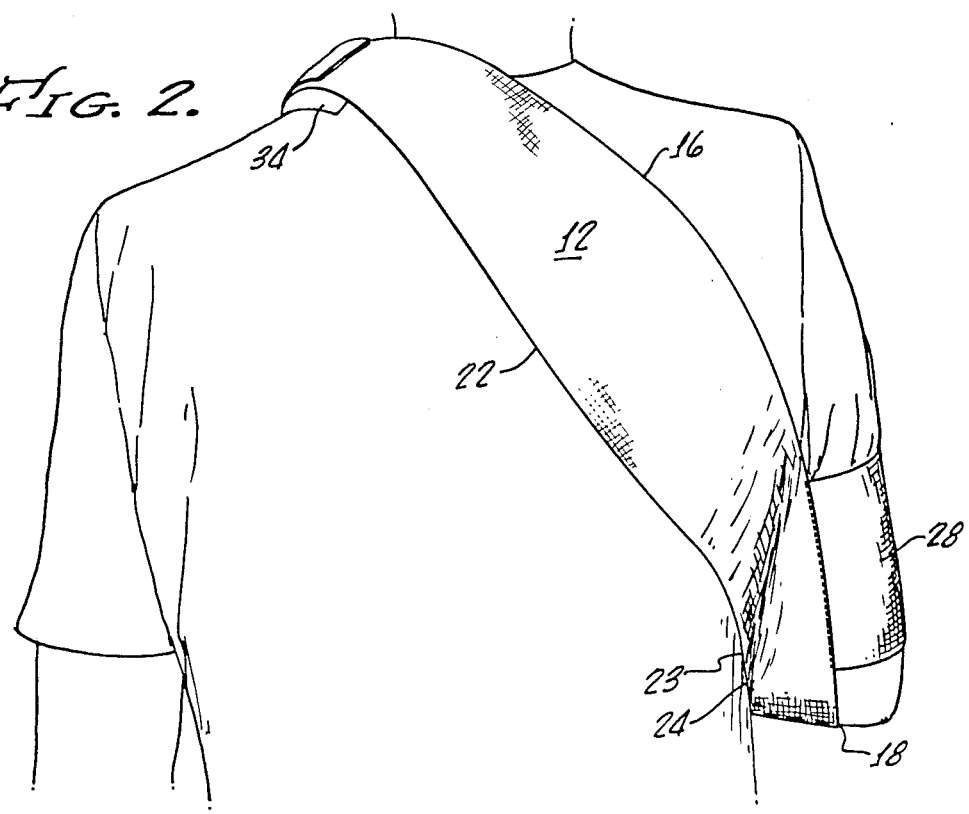
FIG. 2 is a rear elevational view of the showing of FIG. 1.

It is emphasized that part of edge 24 is forwardly adjacent the wrist. From there, the edge 24 bends rearwardly below the forearm, and inclines upwardly toward the right side of the torso of the patient. Referring next to FIGS. 2 and 4, the remaining portion of edge 24 is shown as bending around the torso at a region below point 23.

To describe the above in another manner, one of the edges of the body 10 (designated by the numbers 16-18-21) forms a continuous loop when the apparatus is mounted as shown in FIGS. 1, 2 and 4. The other edge of the body 10 (indicated by the reference numbers 22-24-26) does not merely loop but twists or reverses position at a region between the elbow of the patient and the right side of the patient. At such region, it (portion 24) extends in contact with the patient's side and then inclines downwardly behind the forearm before bending below the wrist region and upwardly-forwardly of the wrist.

Figure 5:
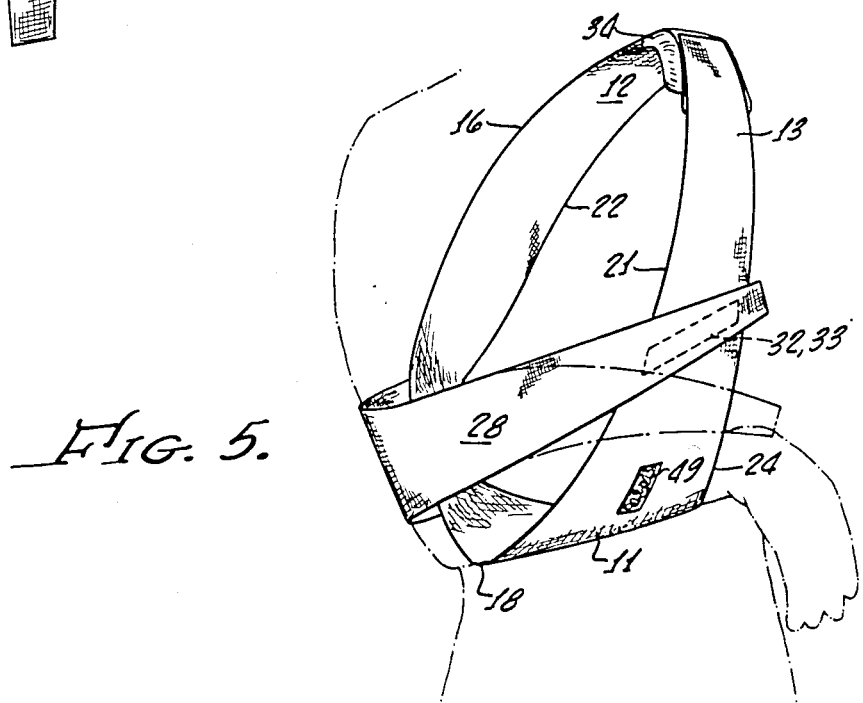
FIG. 5 shows a later part of the sling-mounting procedure.

Referring next to FIGS. 1 and 5, the cloth arm 28 is then bent around the upper arm of the patient, and loop strip 32 is pressed against hook strip 33 at the exact position desired to achieve comfort and relative immobilization.

There is thus provided a very comfortable, effective, attractive arm support. The support or sling is easily moved off and on the patient without disconnecting any of the connected regions, and is then repositioned on the patient so as to resume the desired properly-adjusted and positioned condition. The sling may usually be machine-washed while adjusted, and the connections prevent the long body of the sling from wrapping around the agitator.

To further enhance comfort, a small pillow cushion 34, having hook portions 35 and 36 thereon, is secured to the end of connector region 12 (on the side thereof opposite hook 31) by loop means 38 and 39. Such pillow rests on the patient's shoulder, beneath the hook-loop connection.

Relatively soon after an operation, a second and larger pillow or cushion 41 is secured at the underside of intermediate region 11. The position of pillow 41 is such that it is interposed between the forearm and the stomach region of the wearer.

The forearm may also be secured to the patient's belt 46 by a strap 47 and associated hook and loop fastener means on the strap and on the region 11 of the body 10. Such hook and loop fastener means on strap 47 and on the body are indicated at 48–51.

The strap may pass around the belt, as shown in FIG. 1, or it may pass through one of the belt loops shown at 52. Or, the strap may pass both around the belt and through the belt loop 52.

In the illustrated preferred form, pillow 41 is attached to strap 47, removably, by a hook-loop fastener 52a.

It is pointed out that the strap 47 may be employed without the adjacent pillow or cushion 41, and vice versa.

The identical described sling, except for the pillows, may be used for support of the left arm instead of the right. To accomplish this, the same procedure as is described above is followed, except that the sling is caused to be upside down, and on the opposite shoulder, in comparison to what was previously stated. Thus, the opening part of the sequence is performed by placing the hook means 31 facing downwardly—instead of upwardly—and on the right shoulder instead of the left. It is, however, preferred (for convenience and lack of duplication of VELCRO fasteners for the pillows) that one sling be provided for support of the right arm, and a corresponding (but reverse) sling be provided for support of the left arm. Such corresponding (but reverse) sling has connections for a pillow or pillows.

The foregoing detailed description is to be clearly understood as given by way of illustration and example only, the spirit and scope of this invention being limited solely by the appended claims.

What is claimed is:

1. An arm sling, comprising:
   (a) an elongated flexible element having sufficient length to pass from above one shoulder of the patient, then down across the patient's back, then forwardly adjacent the side of the patient's chest that is not beneath said one shoulder, then beneath the forearm of that arm which is not connected to said one shoulder, and then upwardly, forwardly of such forearm and across the patient's chest to above said one shoulder,
   said element having sufficient width, at least beneath said forearm, to provide comfortable support for said forearm,
   said element being so shaped as to pass solely beneath said forearm, and not receive the elbow or upper arm of said arm, when the sling is mounted on the patient,
   (b) means to connect to each other the end portions of said element (a),
   (c) a second elongated flexible element,
   said second element being connected to said first-mentioned element at a region that is located rearwardly of the upper arm of said arm when said sling is mounted on the patient;
   said second element extending forwardly from said region, then adjacent the outer side of said upper arm, and
   (d) means to connect the outer end portion of said second element to said first-mentioned element at a region above said forearm.

2. The invention as claimed in claim 1, in which said end portions of said element (a) are disposed adjacent said one shoulder, and in which said connector means (b) connects said end portions to each other adjacent said one shoulder.

3. The invention as claimed in claim 2, in which the connection

4. The invention as claimed in claim 3, in which said detachable connection is a hook and loop fastener means.

5. The invention as claimed in claim 1, in which said elongated element comprises two layers of cloth, in which the woof threads of the bottom layer extend longitudinally of said elongated element, and in which the warp threads of the top layer extend longitudinally of said elongated element.

6. An arm sling for supporting a forearm, said sling comprising:
   (a) an elongated element formed of flexible material and having substantial width throughout at least the great majority of its length, said elongated element lying in a single plane prior to mounting on the patient, and not having any pockets or cavities therein adapted to receive a part of the patient's arm, said width of said elongated element being, at least in the vicinity the supported forearm when the arm sling is in mounted condition on a patient, at least as wide as a large portion of the length of the supported forearm,
   said elongated element, when mounted on the patient, passing from above one shoulder of the patient, then down across the patient's back, then forwardly and the forearm of that arm which is not connected to said one shoulder, and then upwardly across the patient's chest to above said one shoulder,
   said elongated element not receiving the upper arm of said arm when said elongated element is mounted on the patient,
   the edge of said elongated element that is lowermost when passing across the back of the patient extending around the side of the patient and then inclining downwardly and in a direction toward the wrist on said forearm of the patient, at a region between said forearm and the patient's body, and then passing forwardly below said wrist and upwardly to said one shoulder at a region spaced from the patient's neck, being that edge most remote from the patient's neck in comparison to the remainder of the element, and (b) means to removably secure to each other the end portions of said elongated element.

7. The invention as claimed in claim 6, in which said end portions are disposed in the vicinity of said one shoulder when said arm sling is mounted on a patient, and in which said removable securing means are disposed adjacent said one shoulder when said sling is thus mounted.

8. The invention as claimed in claim 7, in which said removable securing means comprises hook and loop fastener means.

9. The invention as claimed in claim 6, in which, when said elongated element is in a single plane prior to mounting on a patient, it has a relatively long connector portion and a relatively short connector portion, each such portion extending outwardly from an intermediate region that is relatively wide and is adapted to support said forearm, at least one such connector portion having at the outer end portion thereof a fastener means adapted to be removably secured to the other end portion of said elongated element.

10. The invention as claimed in claim 9, in which said relatively long connector portion has a gradually convex edge that meets a much less gradually convex edge of said intermediate region, said last-mentioned convex edge meeting an edge of said relatively short connector portion, and in which said relatively long connector portion has a gradually concave edge that diverges, relative to said convex edge of said relatively long connector region, in a direction towards said intermediate region, and in which said intermediate region has an edge that meets said concave edge and is relatively steeply convex in comparison to said concave edge, said last-mentioned edge merging with the remaining edge of said relatively short connector region.

11. The invention as claimed in claim 9, in which said elongated element has convex edge portions on opposite sides thereof at the region of said element that engages said forearm of the patient when the arm sling is in mounted condition on the patient, said convex edge portions having their apexes offset from each other longitudinally of said elongated element.

12. The invention as claimed in claim 11, in which indicia are provided at one of said convex edge portions to indicate where the elbow should be positioned.

13. The invention as claimed in claim 6, in which a second elongated element formed of flexible material is connected to said first-mentioned elongated element and extends outwardly therefrom, and in which means are provided to removably secure the outer end portion of said second elongated element to said first-mentioned elongated element.

14. The invention as claimed in claim 6, in which pillow or cushion means are provided between said elongated element and the shoulder of the patient, said pillow or cushion means being removably secured to said elongated element by hook and loop fastener means.

15. The invention as claimed in claim 6, in which pillow or cushion means are provided between the body of the patient and the portion of said elongated element which is behind said forearm, said pillow means being removably secured to said portion behind said forearm of the patient.

16. The invention as claimed in claim 6, in which strap means are provided to extend around the belt or belt loop of a patient to regions of said elongated element adjacent said forearm.

17. A method of supporting an injured or disabled arm of a human, said method comprising:

(a) providing an elongated flexible element having substantial width, throughout at least the majority of its length, said element lying in a single plane and not having any arm-receiving pockets or cavities therein, (b) causing said elongated flexible element to be connected at its end portions so as to form a loop, (c) mounting said looped elongated element on a human patient in such relationship that it passes over one shoulder of the patient, then passes down across the patient's back, then passes forwardly adjacent the side of the patient's chest that is not beneath said one shoulder, then passes beneath the forearm of that arm of the patient which is not connected to said one shoulder, said elongated element passing solely beneath said forearm and not receiving the elbow or upper arm of said arm, and then passes upwardly, forwardly of said forearm, and across the patient's chest to above said one shoulder, characterized in that said mounting is such that one edge of said elongated element inclines downwardly at a position between said forearm and the patient's torso, the downward incline being from adjacent said side of the patient's chest to beneath the region of said forearm relatively near the wrist of said arm.

18. The invention as claimed in claim 17, in which said method further comprises extending an additional elongated flexible element from the portion of said loop that is behind the upper arm connected to said forearm, thence around the outside of said upper arm, and thence forwardly of the patient's torso to a connection point on the portion of said loop that extends upwardly across the patient's chest, and connecting said additional elongated flexible element to said loop portion and said connection point.

19. A method of supporting a forearm of a human patient, said method comprising:

(a) providing a continuous elongated loop element, formed of flexible material, having substantial width throughout at least the majority of its length, said width being, at least in the vicinity of the supported forearm when the sling is in mounted condition on the patient, at least as wide as a large portion of the length of such forearm, said loop element not having any arm-receiving pockets or cavities therein, (b) causing said continuous loop element to pass above one shoulder of the patient, then down across the patient's back, then forwardly along the patient's side beneath the forearm of that arm which is not connected to said one shoulder, and then upwardly across the patient's chest to above said one shouler, (c) causing the edge of said loop element that is lowermost when passing across the back of the patient to extend around said side of the patient and then incline downwardly and in the direction toward the wrist of said forearm of the patient, at a region between said forearm and the patient's body, and (d) causing said edge to pass forwardly below said wrist and upwardly to said one shoulder at a region spaced from the patient's neck in comparison to the remainder of said element.

20. The invention as claimed in claim 19, in which said method further comprises connecting a second element, formed of flexible material, from that portion of said elongated loop element that is adjacent the back of the patient, around the outside of the upper arm of the patient which is connected to said forearm, and then to the portion of said loop element that extends upwardly across the patient's chest.

21. The invention as claimed in claim 17, in which said step (b) is so performed that said elongated flexible element is not twisted.

* * * * *

UNITED STATES PATENT AND TRADEMARK OFFICE
CERTIFICATE OF CORRECTION

PATENT NO. : 4,716,895

DATED : January 5, 1988

INVENTOR(S) : Jean S. Marques and Ernesto D. Marques

It is certified that error appears in the above-identified patent and that said Letters Patent is hereby corrected as shown below:

Column 2, line 4, delete "asjustment" and substitute therefor ---adjustment---.

Claim 3 (column 6, line 31), after "connection", insert ---effected by said means (d) is to that portion of said first-mentioned element that extends across the patient's chest, such connection being detachable.---.

Claim 6 (column 6, line 50), after "vicinity", insert ---of---.

Claim 6 (column 6, line 57), after "and", insert ---beneath---.

Signed and Sealed this

Twenty-first Day of March, 1989

Attest:

DONALD J. QUIGG

Attesting Officer

Commissioner of Patents and Trademarks